(12) United States Patent
Cottrell

(10) Patent No.: US 8,992,222 B2
(45) Date of Patent: *Mar. 31, 2015

(54) RIDGE LAP DENTAL IMPLANT

(71) Applicant: Richard D. Cottrell, Lake Forest, IL (US)

(72) Inventor: Richard D. Cottrell, Lake Forest, IL (US)

(*) Notice: Subject to any disclaimer, the term of this patent is extended or adjusted under 35 U.S.C. 154(b) by 5 days.

This patent is subject to a terminal disclaimer.

(21) Appl. No.: 13/874,622

(22) Filed: May 1, 2013

(65) Prior Publication Data

US 2014/0329201 A1 Nov. 6, 2014

(51) Int. Cl.
*A61C 8/00* (2006.01)
(52) U.S. Cl.
CPC .............. *A61C 8/0077* (2013.01); *A61C 8/0025* (2013.01); *A61C 8/0069* (2013.01); *A61C 2008/0046* (2013.01)
USPC ........................................................ 433/174
(58) Field of Classification Search
CPC .... A61C 8/077; A61C 8/0069; A61C 8/0025; A61C 2008/0046
USPC .................................................. 433/172–176
See application file for complete search history.

(56) References Cited

U.S. PATENT DOCUMENTS

| 5,009,596 | A | 4/1991 | Soderberg |
| 5,030,095 | A | 7/1991 | Niznick |
| 5,078,606 | A | 1/1992 | Soderberg |
| 5,312,255 | A | 5/1994 | Bauer |
| 5,362,236 | A | 11/1994 | Branemark |
| 5,417,568 | A | 5/1995 | Giglio |
| 5,503,558 | A | 4/1996 | Clokie |
| 5,564,925 | A | 10/1996 | Shampanier |
| 5,564,926 | A | 10/1996 | Branemark |
| 5,591,029 | A | 1/1997 | Zuest |
| 5,674,072 | A | 10/1997 | Moser et al. |
| 5,702,695 | A | 12/1997 | Clokie |
| 5,785,525 | A | 7/1998 | Weissman |
| 5,863,201 | A | 1/1999 | Lazzara et al. |
| 5,879,161 | A | 3/1999 | Lazzara |
| 5,890,902 | A | 4/1999 | Sapian |
| 5,947,735 | A | 9/1999 | Day |
| 6,164,969 | A | 12/2000 | Dinkclacker |
| 6,217,333 | B1 | 4/2001 | Ercoli |
| 6,283,754 | B1 | 9/2001 | Wohrle |

(Continued)

FOREIGN PATENT DOCUMENTS

| WO | WO 01/49199 A2 | 7/2001 |
| WO | WO 01/49199 A3 | 7/2001 |

OTHER PUBLICATIONS

Suk-Won Lee and colleagues, Influence of Etched Microgrooves of Uniform Dimension on in Vitro Responses of Human Gingival Fibroblasts, Clin. Oral Imp. Res, 20, 2009; p. 458-466.

J.J. Cawood and R.A. Howell, Reconstructive Preprosthetic Surgery, 1. Anatomical Considerations, Int'l Journal Oral Maxillofacial Surgery, 1991:20, 75-82.

(Continued)

*Primary Examiner* — Ralph Lewis
(74) *Attorney, Agent, or Firm* — Law Offices of Eugene M. Cummings, P.C.

(57) ABSTRACT

An asymmetrically placement designed to preserve bone by having the coronal aspect being compatible with the bony anatomy at the time of tooth extraction. The implant may be of either a single or two state design. By modifying the top of the implant fixture to partially mimic the bony anatomy at the time of the extraction more crestal bony anatomy can be preserved and bone growth encouraged.

14 Claims, 10 Drawing Sheets

(56) References Cited

U.S. PATENT DOCUMENTS

| | | | |
|---|---|---|---|
| 6,655,961 | B2 | 12/2003 | Cottrell |
| 6,672,872 | B2 | 1/2004 | Cottrell |
| 6,854,972 | B1 | 2/2005 | Elian |
| D511,833 | S | 11/2005 | Wohrle |
| 7,264,469 | B2 | 9/2007 | Abarno |
| 7,270,542 | B2 | 9/2007 | Cottrell |
| 7,329,124 | B2 | 2/2008 | Mundwiler et al. |
| 8,066,511 | B2 | 11/2011 | Wohrle et al. |
| 2003/0064349 | A1 | 4/2003 | Simmons, Jr. |
| 2003/0120279 | A1 | 6/2003 | Hansson |
| 2007/0148622 | A1 | 6/2007 | Gogarnoiu |
| 2010/0330533 | A1* | 12/2010 | Cottrell ......................... 433/174 |

OTHER PUBLICATIONS

Suk-Won Lee and colleagues, Influence of Microgroove Dimension on Cell Behavior of Human Gingival Fibroblasts Cultured on Titanium Substrata, Clin. Oral Impo, Res. 20, 2009; p. 56-66.

The CORE-VENT Implant System, The Journal of Oral Implantology, vol. X No. 3, 1982.

Marco Degidi and colleagues, Peri-Implant Collagen Fibers Around Human Cone Morse Connection Implants Under Polarized Light: A Report of Three Cases, The International Journal of Periodontics & Restorative Dentistry, vol. 32, No. 3, 2012.

Marco Degidi and colleagues, Immediately loaded titanium implant with a tissue-stabilizing/maintaining design ('beyond platform switch') retrieved from man after 4 weeks: a histological and histomorphometrical evaluation. A case report, Clin. Oral Impl. Res. 19, 2008 / 276-282.

* cited by examiner

RIDGE LAP DENTAL IMPLANT

CROSS-REFERENCE TO RELATED APPLICATION

This application claims the benefit of priority under USC §119(e) of provisional application No. 61/641,361, filed May 2, 2012, entitled "Ridge Lap Dental Implant", hereby incorporated by reference herein.

BACKGROUND OF THE INVENTION

The present invention relates generally to dental implants, and more specifically to a dental implant having an improved coronal configuration to take advantage of the presenting bony topography that is often present immediately following tooth extraction prior to any healing or remodeling process. This ridge lap dental implant is suitable, but not limited to, both immediate and delayed implant placement in the upper anterior region of the mouth.

Dental implants are used in place of missing natural teeth to provide a base of support for single, multiple teeth or full arch prosthetics. These implants generally include two components, the implant itself and the prosthetic mounting component referred to as an abutment upon which the final prosthesis is installed. The implant has apical and coronal ends, whereby the coronal end accepts the base of the prosthetic abutment using connection mechanisms of different designs. One such mechanism is a deep female conical receptor with an internal alignment or anti-rotational element such as a hex, double hex, spline or other single/multi sided arrangement used for prosthetic alignment and anti-rotational stability. Deep female conical connections have been shown to be the most stable mechanisms by preventing micro movement between the implant body and the abutment under normal loading conditions. It has been suggested that preventing micro movement is one of the key factors required for crestal bone maintenance.

Dental implants are used in place of extracted (and/or missing) natural teeth as the base of support for an abutment and final prosthesis to restore normal oral function. But once a tooth is no longer present, the bone from which the tooth originated heals and is forever changed. Accordingly, while dental implants should be designed to take into account the healing process of bone after tooth loss, this is seldom the case. In fact, dental implant designs for the most part are not designed to take into consideration the presenting bony topography prior to implant placement. In fact, it is common for surgeons to modify or flatten the bone to suit the implant configuration rather than design the implant to suit the presenting anatomy.

In practice, the implant body is surgically inserted in the patients jaw and becomes integrated with the bone. This can be done immediately at the time of tooth extraction or in a delayed manner allowing healing and remodeling to occur first. More specifically, the implant body is screwed or pressed into holes drilled in the respective bone or the apical end of extraction socket is prepared to accept the insertion of a dental implant immediately. The surface of the implant body is characterized by macroscopic and microscopic features that aid in the process of osseointegration. Once the implant is fully integrated with the jaw bone or in some cases at the time of insertion the abutment is ready to be mounted. For two-stage implant designs, the abutment passes through the soft tissue that covers the coronal end of the implant after healing and acts as the mounting feature for the prosthetic device to be used to restore oral function. Implants of the single-stage design extend at least partially through the soft tissue at the time of surgical insertion. The coronal end of the single stage implant body acts as a built-in abutment with the margin of the coronal collar usually being employed as the margin of attachment for the prosthesis used to restore oral function. These components, the implant and abutment, are typically fabricated from titanium or titanium alloy as well as zirconia based, alumina based or sapphire based ceramics. In some instances, ceramics and metals are combined to make a single component, though this is usually limited to the abutment component of the implant system. Titanium zirconium alloys and in the future nano structure titanium could become used due to significant increased strength.

Implant designs have gone through a considerable amount of trial and error in an attempt to deal with the issue of the bone not healing evenly once a tooth has been extracted. It has been found that bone heals based on the principles of bone biology, surrounding bony and soft tissue anatomy, as well as blood supply to the area. To a certain degree, bone healing and/or remodeling is also influenced by the placement and subsequent loading of an implant fixture. Only a limited number of studies have been conducted regarding bone loss patterns following tooth loss. Two such studies, one by Pietrokovski and Massler, published in the *Journal of Prosthetic Dentistry* in 1967; and another by Cawood and Howell, was published in the *International Journal of Oral and Maxillofacial Surgery* in 1991, are included as reference.

One can construe from these studies that for a time period as short as several months, the highest point of bone anatomy is toward the lingual side of extracted teeth after healing with considerably more remodeling/resorption on the buccal aspect. Due to the natural bony contours in the anterior area of the upper jaw, this healing pattern, often referred to as facial collapse of bone, is more immediate there than in the posterior upper and lower jawbones.

In the 1980's one of the most commonly placed implant designs was the Branemark type dental implant. As with most traditionally designed implants, and a number today, the Branemark type fixture relied on a flat to flat matting surface perpendicular to the long axis of the implant body as the mating interface when joining the implant and the abutment together. This design usually displays a bone loss pattern described as a cupping of the bone at the coronal end of the implant usually down to the first major thread on the implant body. This bone loss pattern usually stabilizes after about one year of function with vertical bone loss of approximately 1.5 to 2.0 mm.

There are dental implants systems that typically do not demonstrate a cupping bone loss pattern. Two such implant systems are by Astra Tech and Ankylos. Both of these implants have an internal female conical connection and do not rely on flat to flat mating surfaces at the implant/abutment interface. However, the Ankylos surgical protocol suggests placing the implant two millimeters below the crest of bone because the philosophy is to allow bone to grow over the top of the implant and cover at least part of the platform at the coronal aspect of the fixture which extends outward from the abutment conical connection penetration. The Astra protocol is to place the implant at bone level or very slightly below and have the bone integrate apically from the most apical aspect of the reverse bevel at the coronal aspect of the Astra Tech Profile fixture.

Astra Tech now offers implants with a sloping coronal contour such that the height of lingual bone crest is engaged and preserved in sloped ridge situations. In particular, U.S. Pat. No. 7,270,542, to Cottrell, incorporated herein by reference, is directed to such a modified sloped top dental implant fixture. Dental implants made to these design specifications make it easier for surgeons to place implants ideally and maintain the bony topography after healing remodeling has occurred. This modified sloped top dental implant is commercially available as the Astra Tech Profile, and is generally illustrated by FIG. 1 herein.

The Astra Tech system mentioned above has essentially been modified to develop a dental implant with a sloping coronal contour that is convex when viewed in FIG. 1. Much of the success of this implant is credited with Astra Tech design having a combination of a rigid conical abutment connection and the presence of coronal stress reducing micro threads on the implant body which in combination greatly reduce, and in most cases, eliminate the aforementioned bone loss patterns. The reverse bevel at the top of the implant inherent in the design of fixtures with a deep conical connection may also be important as well. It has been proposed, and possibly validated by Degidi in the *International Journal of Periodontics and Restorative Dentistry* 2012 June: 32(3): 323-8, and by Degidi in the *Clinical Oral Implant Res.* 19, 2008, 276-282 that the circular connective tissue fibers at the base of the implant gingival complex, that develop above the implant once the final abutment is installed, may help prevent apical soft tissue migration acting as a mechanical support mechanism. Both Degidi references are hereby incorporated by reference herein. The Ankylos design has bone growing over the platform at the top of the implant but must be placed deeper below the level of the most apical crestal bone available in order for bone to grow over the top of the fixture. The Ankylos implant has more of a coronal shoulder than Astra's reverse bevel in order to maintain adequate wall thickness for the Ankylos approximate six (6) degree internal conical connection but the shoulder essentially has the same effect with regard to the circular connective tissue fibers. The present disadvantage is that in many instances one side of the implant platform which is, as mentioned above, relatively flat has to be buried deeper than necessary for this overgrowth of bone to occur. This is particularly true in the upper anterior region of the mouth where the Ankylos fixture must be significantly buried on the lingual aspect due to the presenting anatomy in that region, see FIG. 7 herein.

However, while the sloped top implant works very well with extraction sites that have been allowed to heal, and the implant placed following the delayed protocol, it may not be the ideal design when implanted immediately following tooth extraction. Certainly sloped top fixtures work better than traditional flat topped fixtures in the upper anterior region of the mouth, but the contours are still not exactly ideal for immediate placement. In order to compensate for the mismatch between the extraction socket topography and the sloped top design, Cottrell has applied for a patent (application Ser. No. 12/494,510) on a design that has a modified coronal contour. This design calls for the mesial length to be greatest and the buccal length shortest with the lingual and distal dimensions intermediate in length. Viewed from the mesial aspect the coronal contour is convex, as is the contour of the Profile fixture in FIG. 1 as referenced above. The contours of the asymmetric fixture do not perfectly mimic the CEJ contours of the upper anterior teeth because implants are undersized relative to the extraction socket following the immediate placement protocol and as a result some remodeling is going to occur. While the design takes into consideration the height of the lingual side of extraction socket in the upper anterior region it does not follow the contours of the interproximal bone levels which are even higher. The Asymmetric Design, as it is called, tries to anticipate the bone remodeling upon healing remodeling and still preserve some of the interproximal bone height. Unfortunately, while the Asymmetric implant design is ideal in approach it does present a problem. Being asymmetric in character, different fixtures are required for the upper right and upper left anterior regions in the mouth and different fixtures for the upper/lower right and upper/lower left quadrants of the mouth. Consequently, there is concern that potential surgical and inventory complications could arise for the surgeon.

At the coronal aspect of a dental implant placed immediately in the upper anterior region of the mouth a gap is generally present on the mesial, distal and buccal sides on the fixture as only the apical end is firmly anchored in bone and the lingual side ideally but not always in contact with the bone. Accordingly, as mentioned before some remodeling is going to take place as these gaps fill in with new bone. The objective of the asymmetric concept was to design the coronal contour of the dental implant that anticipates how this will occur when immediate implant placement protocol is undertaken. A compromise must be established between the bony contours that exist around the coronal contour of the extraction socket and the contours of the asymmetrical dental implant which best takes into account the angulation that the implant must follow in the extraction socket while anticipating the remodeling process compared to the delayed implant placement protocol.

However this particular improvement caused issues because different fixtures would be required in the upper anterior for the upper right and left sides of the mouth and for the upper left/lower right and upper right/lower left quadrants of the mouth. Additionally, Astra Tech was recently purchased by Dentsply International, who already owns the Ankylos system. As mentioned above, the recommended Ankylos protocol is to bury the implant. So the general object of the present invention is to offer a grand compromise. If Ankylos suggests burying the top of the implant 2.0 millimeters below the lowest level of the available bone, the present disclosure is suggesting there is a way to contour the top of the fixture to prevent burying aspects of the Ankylos shoulder deeper than Ankylos presently recommends, especially on the lingual aspect in the upper anterior region of the mouth. Further the present disclosure would satisfy Astra Tech and others main objection since only one implant design for upper right and left sides of the mouth and all posterior quadrants would be required. Also, since Ankylos buries the top of the fixture having the implant slightly longer on the mesial than the distal isn't as important. While it is more of an issue for a bone level design like Astra Tech's in reality many surgeons bury those fixtures to a degree as well, so being perfectly coronally contoured as the asymmetric design suggest maybe isn't as important for bone level designs as Astra Tech's either. Accordingly, what is being disclosed is a smooth, continuously contoured coronal profile without abrupt change in direction such that the longest mesial and distal lengths are equal, the buccal lengths are shorter than their most adjacent mesial and distal lengths and the lingual lengths are shorter than their most adjacent mesial and distal lengths such that the shortest lingual length is longer than the shortest buccal length. Further, when viewed from the mesial or distal, the outer bone engaging aspect of the coronal contour of the outer aspect of the implant fixture is convex. It is also proposed that in the most ideal configuration that all corresponding mesial and distal lengths, corresponding lingual lengths as well as corresponding buccal lengths are equal. In this case, the meaning of corresponding would be the same lengths in a mirror image reflection such that if the implant were sectioned in the middle buccal to lingual both sides would be identical but a mirror image of one another.

The body of the implant can be a tapered or straight walled fixture. Going forward this contour will be referred to as the Ridge Lap design as the coronal contour mimics the underside of a ridge lap pontic in a bridge prosthesis. Anyone skilled in the art will appreciate that as long as the mesial and distal greatest lengths are equal that they do not necessarily have to be correspondingly equal as herein defined. The same would be true for the buccal and lingual lengths as corresponding lengths could be slightly unequal. However, this would result in asymmetry and void one objective of the Ridge Lap concept but done in a way that is not detectable clinically. In other words, the mesial half and the distal half of the coronal contours being mirror images of one another. The proposed Ridge Lap coronal contour, while not as ideal as the Asymmetric Design, will still help overcome the challenge of preserving at least some of the interproximal bone height and allow Ankylos surgeons to reduce the depth of fixture placement, particularly on the lingual aspect as shown in FIG. 8, but still allowing bone overgrowth onto the shoulder of the fixture. The Ridge Lap design allows the top of either the Astra Tech or Ankylos type implant design to better follow the surrounding bony contours in the upper anterior region of the mouth in particular at the time of extraction and still be easy for the surgeons to place clinically.

Interestingly, the Ridge Lap contour also has application for single stage implants as well. Straumann is now the largest implant company in the world and at least 50% of their sales are single stage implants only introducing a bone level fixture into the marketplace in the past 3-4 years. Single stage implants with a level coronal platform do work reasonably well in the upper posterior region of the mouth but require extremely accurate placement by the surgeon. Since the bone and soft tissue in the upper posterior is often flat, the top of the single stage implant works well to provide a margin for the final prosthesis. However, in the lower posterior, the anatomy more often than not shows buccal bone remodeling and the level of the bone and soft tissue on the buccal aspect is more apical. The Ridge Lap contour gets its name by following the underside of a ridge lap pontic of a fixed bridge prosthesis. Contouring the top of a single stage implant to follow the same contour would overcome some of the issues that single stage implants present in the lower posterior. Namely they are often buried deeper than desirable so the top of the implant is not exposed on the buccal aspect. This buries the lingual side of the implant and it can be at times difficult to remove the final luting cement. In years past, cement contamination down the side of the implant was overlooked but recently that has become a hot topic of discussion. Numerous clinicians have presented cases showing bone loss in implant cases where cement has been found to be a contaminant. This has been one of the reasons custom abutments of bone level implants have become so popular since the margin for the final prosthesis is machined to follow only slightly below the soft tissue contours. Therefore, the Ridge Lap contour as applied to a single stage implant as shown in FIG. 10 is considered to be very desirable.

Accordingly, it is the general object of the present Disclosure to provide an implant with a coronal contour that will do much of what Cottrell's Asymmetric Design would accomplish while simplifying the design to have equal mesial and distal contours.

It is a further object of the present disclosure to overcome the challenge of maintaining at least some of the interproximal bone height that has to date been difficult to maintain.

It is another object of the present disclosure to provide a modified dental implant design combining the elements that are known to work in overcoming crestal bone loss such that the problems related to immediate implant placement with respect to maintaining the natural bony topography present at the time of tooth extraction can at least be partially accomplished.

It is a more specific object of the present disclosure to enable single state implants to be placed in a delayed manner in healed sites that exhibit buccal bony remodeling requiring that the buccal aspect of the implant to be placed more apically to follow the soft tissue topography without burying the lingual aspect of the implant.

These and other objects, features and advantages of the present invention will be clearly understood through a consideration of the following detailed description.

SUMMARY OF THE INVENTION

A dental implant having a longitudinal body with an outer bone engaging surface, apical and coronal ends, and mesial, distal, buccal and lingual sides. The body having lengths along its outer surface that include mesial, distal, buccal and lingual lengths when positioned within a jawbone. The coronal end has an inner female conical shape with a coronal bevel having proximal and distal aspects. The bevel has a bone engaging contour to provide a continuous asymmetric coronal contour without any abrupt changes in direction such that the longest mesial and distal lengths are equal, the buccal lengths are shorter than their most adjacent mesial and distal lengths, and the lingual lengths are shorter than their most adjacent mesial and sistal lengths such that the shortest lingual length is longer than the shortest buccal length. And, when viewed from the mesial or distal aspects, the bone engaging coronal contour is convex without abrupt interruption in direction from a most lingual to a most buccal point.

DESCRIPTION OF THE PREFERRED EMBODIMENTS

Figure 1:
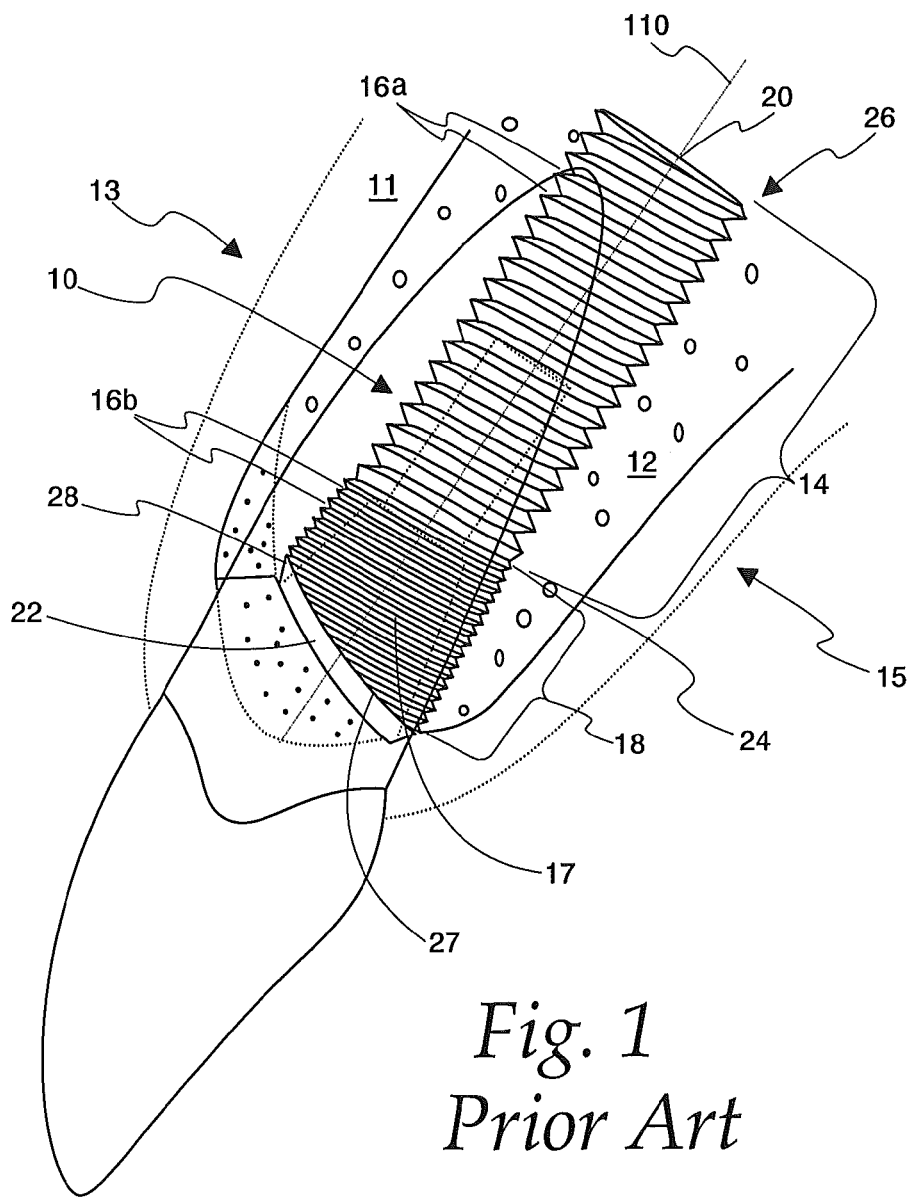
FIG. 1 is a side perspective view of a prior art sloped top dental implant.

Referring now to the Figures, and in particular FIG. 1, the aforementioned prior art sloped top implant 10 is illustrated implanted within the jawbone 12. The body of the implant 10 is preferably, but need not be, comprised of screw threads to aid in the implantation process. The lower portion 14 of the implant body includes larger threads 16a than the smaller threads 16b of the upper portion 18. It has been found that the smaller threads significantly reduce stress forces transmitted to bone and helps to preserve cortical bone. They also increase the fixture strength by maintaining wall thickness without changing the outer dimension of the implant, compared to using larger and deeper threads in the same area of the implant. The deep threads of current practices tend to dig into the body of the implant and weaken it. In any event, other means may be used on the outside surface of the implant 10, and specifically upper portion 18, such as small grooves or laser etched ridges affixed to the implant within the bone 12, with the apical end 20 securely anchored. The surface of the implant 10 may be textured/coated in differing ways to promote osseointegration. FIG. 1 further illustrates the soft tissue 11 over laying the bone 12, the buccal side 13, the lingual side 15, the conical interface 17, and the convex bone engaging contour 27 of the implant 10.

The basic concept of the prior art implant 10 of FIG. 1 is the contouring or sloping of the coronal 22 or top of the implant fixture such that the lingual bone 24 can be engaged at a more coronal level and preserved. This coronal contour can be a straight line or a convex contoured design so long as the lingual bone engaging side 26 of the implant body (which would become the lingually oriented side of the implant fixture) is longer in the apical-coronal bone engaging dimension than any other apical-coronal bone engaging dimension. The reverse bevel 28 at the coronal aspect 22 of the implant body is necessary to provide additional wall thickness for the internal female conical connection 17. The angle of this reverse bevel can continuously vary so that the bone engaging surface 27 does not necessarily follow the exact contours of the most coronal contour 22 of the implant.

As previously discussed, while the sloped top design of the prior art of FIG. 1 works very well with extraction sites that have healed, and the delayed placement protocol followed, it may not be the ideal design when implanted immediately following an extraction. For such immediate implantation, the present invention provides for a more exaggerated convexity of the top design. In particular, and referring to FIG. 2, the more coronally contoured end 40 of the implant 30 and especially the convexly contoured bone engaging coronal interface 41 is illustrated within jawbone 12. The body of the implant 30 is preferably, but need not be, comprised of screw threads to aid in the implantation process. The lower portion 32 of the implant body includes larger threads 34a than the smaller threads 34b of the upper portion 36. Other means may be used on the outside surface of the implant 30 affixed to the implant within the bone 12, so long as the apical end 38 thereof is securely anchored. The surface of the implant 30 may be textured/coated in differing ways to promote osseointegration.

Figure 2:
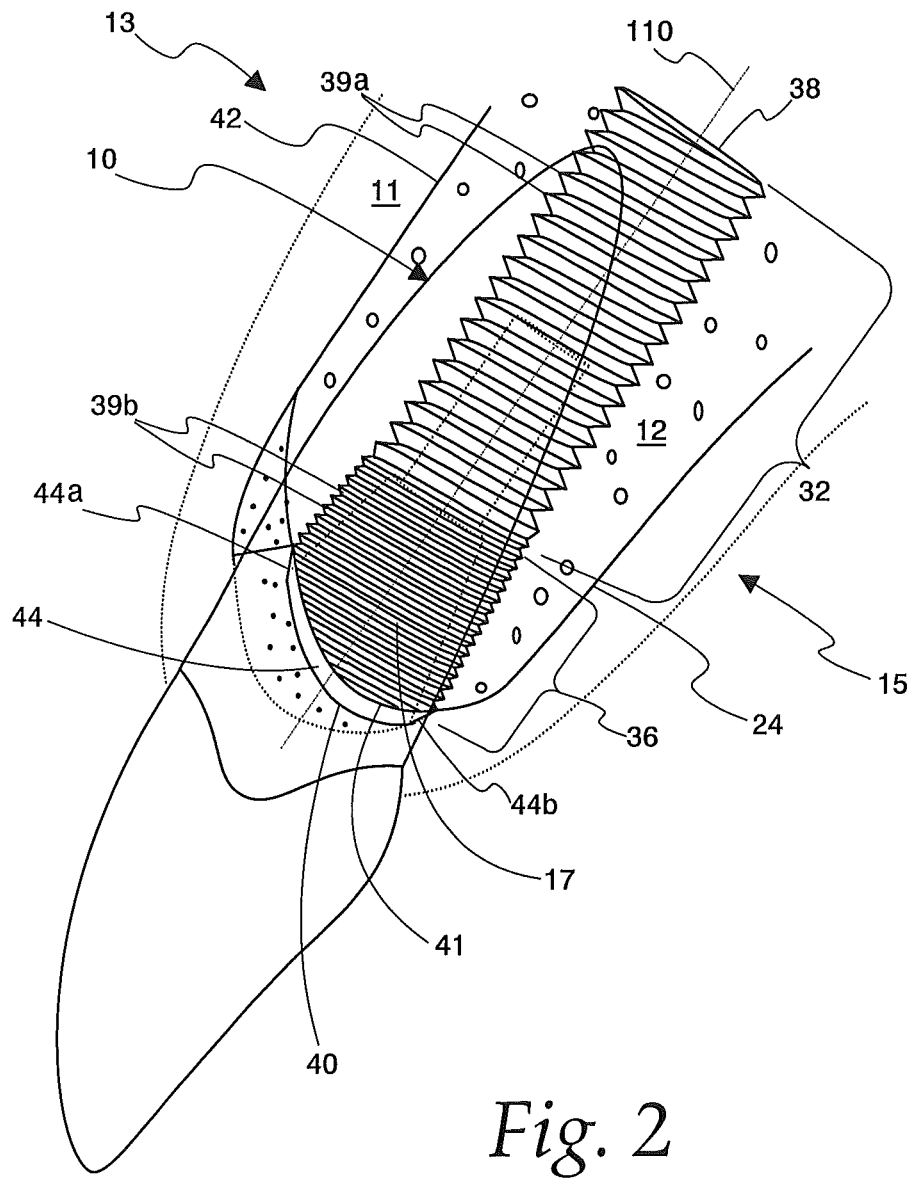
FIG. 2 is a side perspective view of the Ridge Lap implant of the present disclosure.
Figure 8:
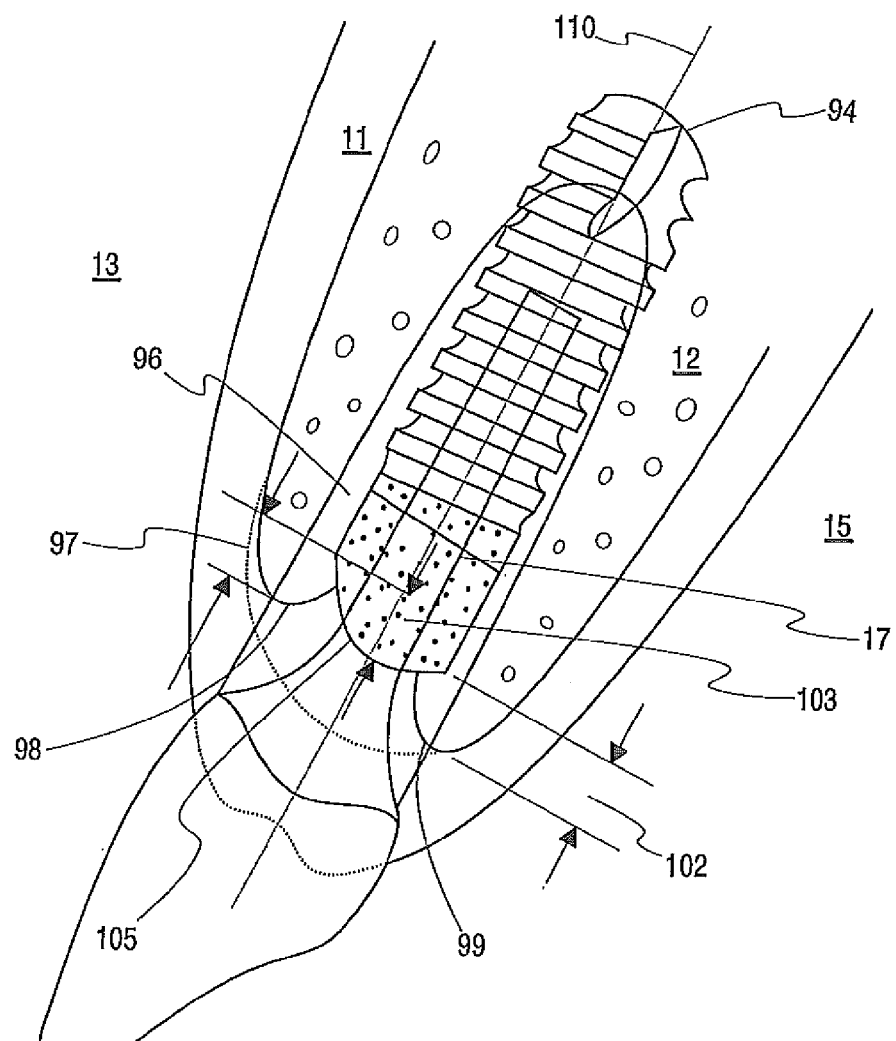
FIG. 8 is a cross sectional view of an Ankylos implant reflecting the Ridge Lap design modification and reflecting the Ankylos placement philosophy.

The basic concept of the implant of the present invention is the convex contouring of the coronal or top 40 of the implant fixture such that the bone engaging contour 41 at the most apical level of the reverse bevel 44 anticipates the crestal remodeling as gaps between the extraction socket walls and in the implant fixture fill in with new bone and then preserve that topography. The coronal end is contoured such that the corresponding greatest lengths of the implant body are equal on the mesial and distal aspects when inserted into the jawbone, the buccal lengths are shorter than their most adjacent mesial and distal lengths with the corresponding buccal lengths being equal and the corresponding lingual lengths longer than their corresponding buccal lengths but less than their adjacent mesial or distal lengths. The reverse bevel 44 at the coronal aspect 40 of the implant body also provides additional wall thickness for the internal female conical connection. This reverse bevel can be of a constant or variable angle relative to the fixture's long axis. FIG. 2 shows that the bevel 44 can continuously vary, for example, by having a steeper angle on the buccal side 44a than the lingual side 44b. In the case of the Ankylos type implant, the bevel can be of a very extreme angle forming almost or at 90 degrees with the fixture long axis resulting in a continuous 90 degree shoulder. However, a variably angled shoulder for the Ankylos design as shown in FIG. 8 is a more preferred coronal contour.

Figure 3:
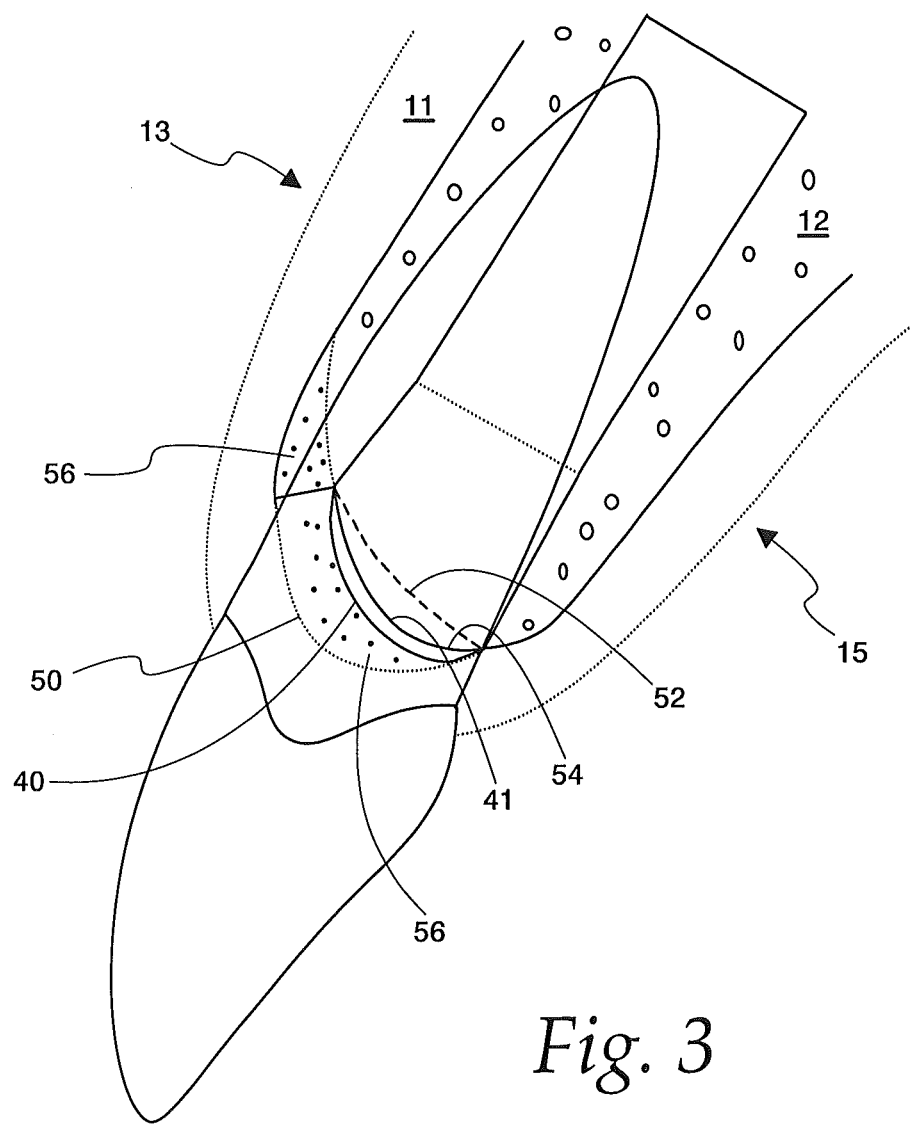
FIG. 3 is a side view of a comparison of the implant contours of FIGS. 1 and 2.

The Ridge Lap implant of FIG. 2 and the prior art sloped top or Profile implant of FIG. 1 are compared in FIG. 3. The contour of bone 50 is what is found around and between the natural tooth. Comparing this natural contour 50 with the delayed protocol healing bone topography 52 it is hoped that an intermediate contour 54 can be maintained that follows the proposed bone engaging contour 41 at the coronal aspect of the Ridge Lap implant. Contour 52 is the contour of a healed ridge following tooth extraction and is more specifically the contour in the middle of a single extraction site between two upper anterior teeth. However, a dental implant, while generally not as wide as the extracted tooth to be replaced does extend mesial and distal from the middle of the extraction socket. Some of the bone between the midline of the extraction socket and the contour around the natural tooth being extracted may be maintained or even regenerated if lost due to pathology using growth factors. In other words, not all of the bone noted by 56 will necessarily be resorbed. And, even if it has been lost due to pathology it may be possible to be partially regenerated utilizing recent advancements in bone grafting techniques, especially those involving growth factors that enhance healing and reduce the amount of bony remodeling. Therefore, it is proposed that an immediate contour 54, can be achieved or maintained on a reasonably consistent clinical basis by experienced clinicians. It is further proposed that this bone can be maintained if a dental implant with a proven track record of bone level maintenance such as the AstraTech design is used and the proposed corresponding Ridge Lap coronal configuration is incorporated therein.

Figures 4, 5:
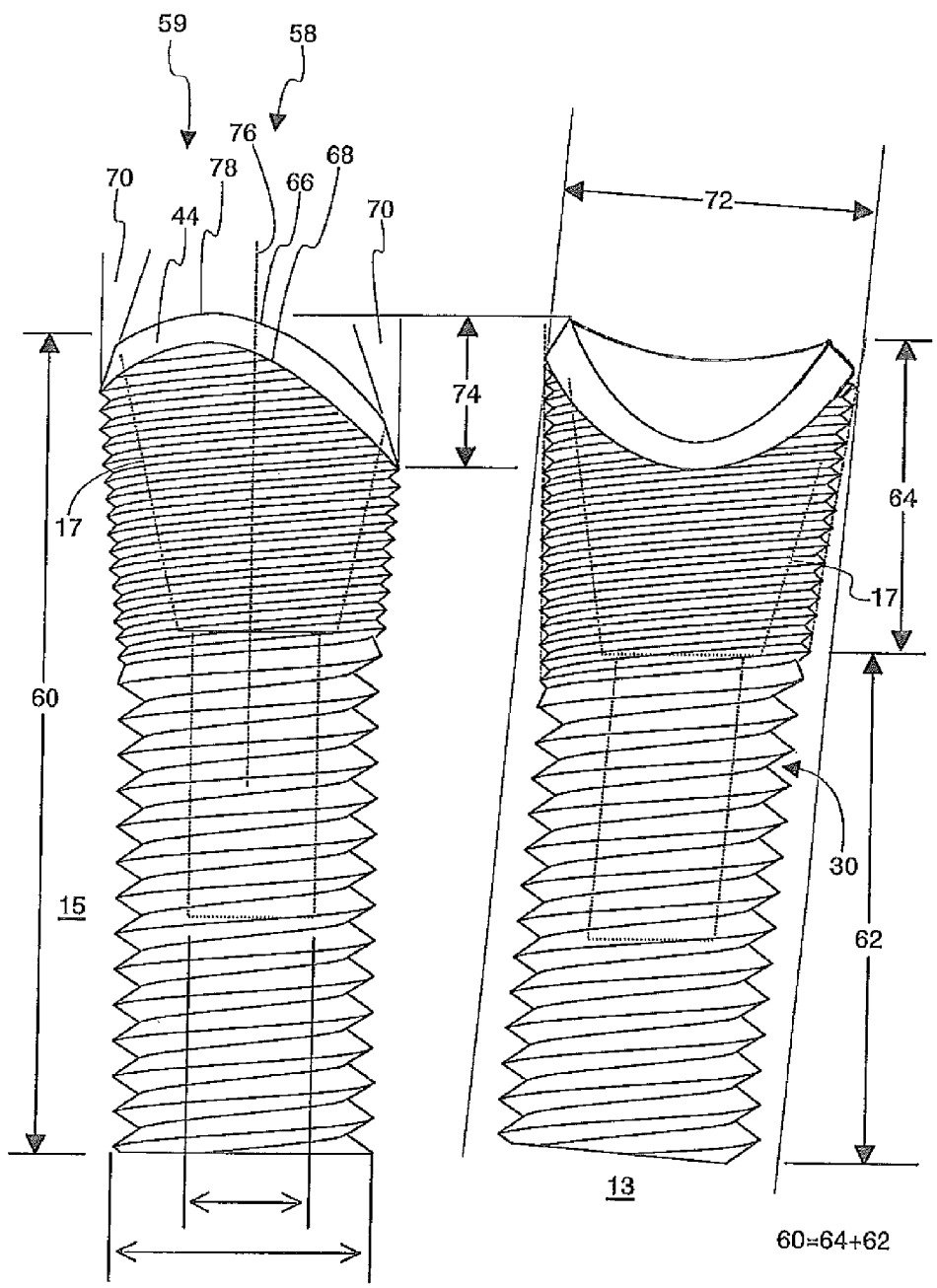
FIG. 4 is a side elevated view of the Ridge Lap implant of the present disclosure.
FIG. 5 is a frontal view of FIG. 4.

More particular dimensions of an embodiment of the present disclosure are illustrated in FIGS. 4 and 5. The side view of FIG. 4 shows the general length 60 of the implant 30. The overall lengths on the bone engaging surface of the implant varies depending upon the general side of the implant. In particular, the length 60 of the implant is greatest and correspondingly equal on the mesial 58 or distal side 59 when inserted into the human jawbone, represented by the mesial view of FIG. 4 and is shortest on the generally buccal side 13, or the view of FIG. 5. The implant lengths on the lingual side 15 are shorter than their most adjacent mesial and distal lengths and longer than their corresponding lengths on the buccal aspect 13.

It is the more apical or outer aspect 68 of the reverse bevel 44 on the coronal aspect of the fixture 30 that determines the length of the bone engaging surfaces upon insertion into the human jawbone for the different sides of the implant. While the coronal design is a bevel 44 which includes a top 66, a bottom 68 and variable angle X 70, it is the bone engaging surfaces that remains the crux of the disclosure. In that regard, although the width 72 of the top is important, it is height 64 of the top which affects the overall length 60 and therefore the bone engaging surfaces of the implant. It is important to note that while the greatest overall lengths of the implant are on the mesial and distal sides when implanted in the jawbone, the greatest length is not necessarily in the center of the mesial or distal aspect of the fixture. More particularly, FIG. 4 shows the centerline 76 of the implant with the longest point 78 to the tongue or lingual side 15 of center. FIGS. 4 and 5 further show the height 74 of the highest point of the top bevel 66 to the lowest point of the bottom bevel 68.

Figure 6:
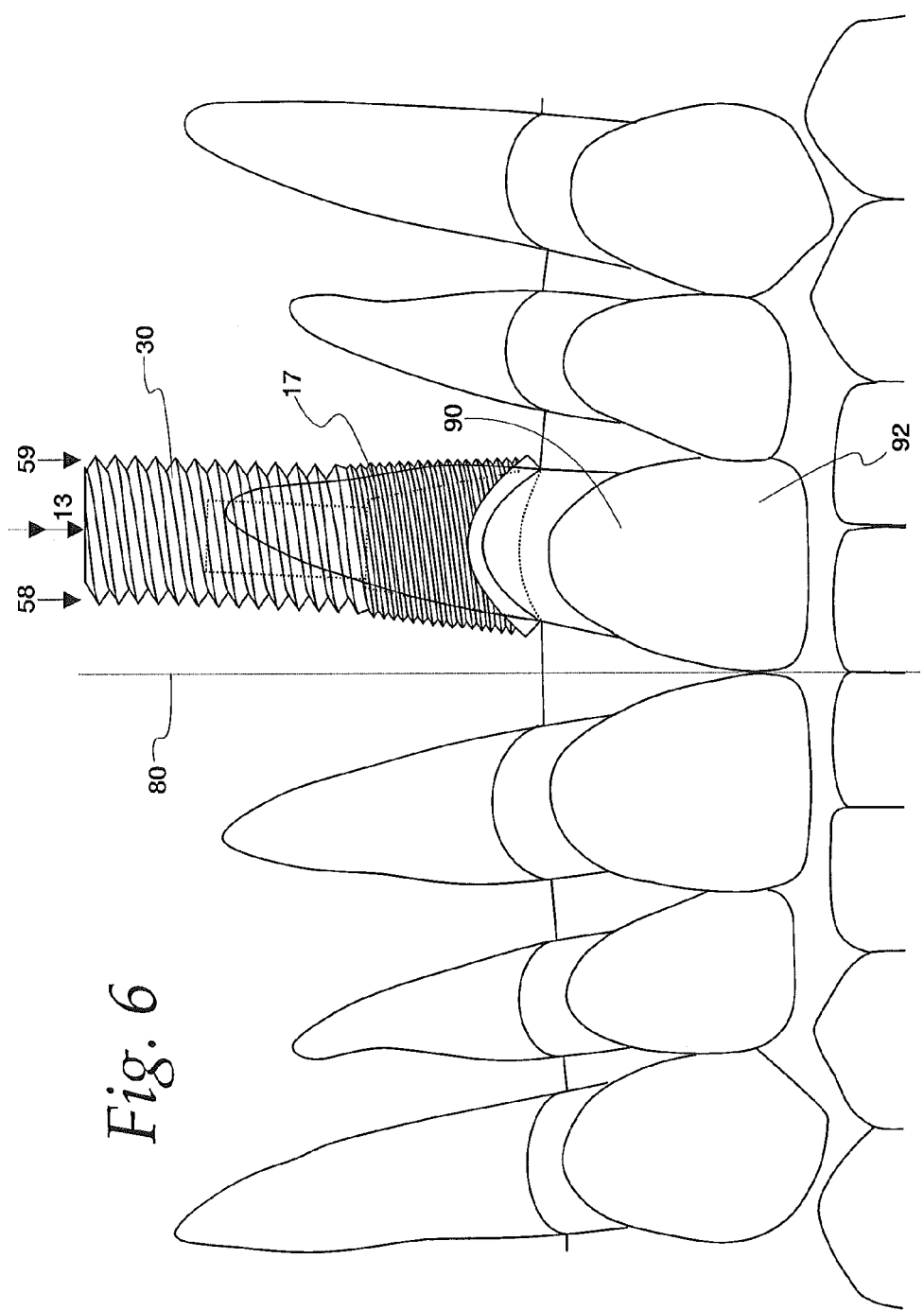
FIG. 6 is a frontal view of the Ridge Lap implant of the present disclosure reflecting the Astra Tech design and placement philosophy.

As previously discussed, these dimensions may need to be adapted to the particular position of the implant with the jawbone. Turning now to FIG. 6, an implant utilizing the principles of the present invention is shown inserted within the maxilla just distal to the jaws centerline 80. This placed implant shows the relative lengths of the different bone engaging sides of the implant body. For example, the lengths are now equal and greatest on the generally mesial side 58 and distal side 59 and shortest on the generally buccal side 13; while the lingual lengths on the lingual side 15 are shorter than their most adjacent mesial 136 and distal length 138 and longer than their corresponding buccal lengths.

FIG. 6 further illustrates other important features of a tooth prosthesis. For example, once the implant 30 is positioned, the abutment 90 is inserted into the conical interface 17 and the subsequent crown 92 can be placed.

Figure 7:
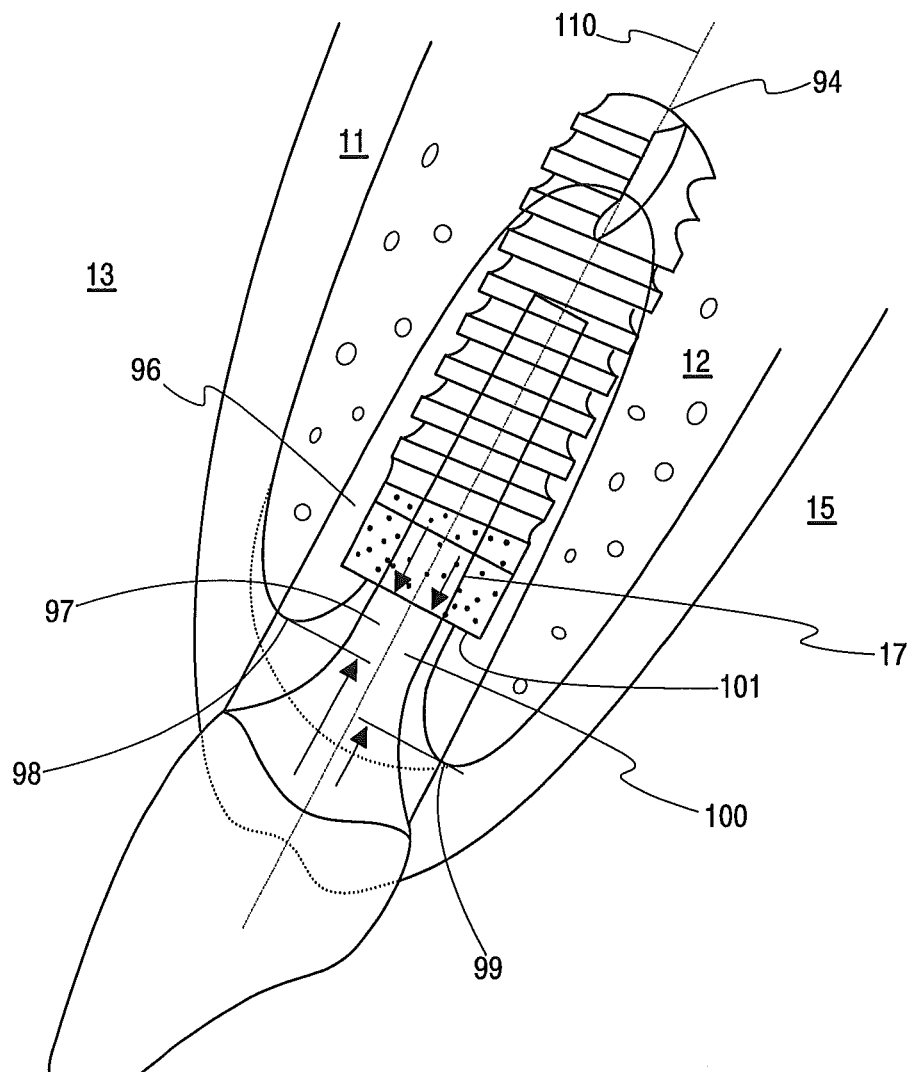
FIG. 7 is a side perspective view of a prior art Ankylos implant reflecting the Ankylos design and placement philosophy.

FIG. 7 shows an Ankylos implant 94 placed in an immediate extraction socket 96 reflecting the Ankylos placement protocol of submerging the implant approximately 2.0 millimeters 97 below the most apical bone level 98. Bone crests 98 and 99 show bone growing over the shoulder 101 of the implant. The dimension 100 is included for reference to be compared to the similar dimension 102 of the present disclosure in FIG. 8. The conical interface 17 of the Ankylos type implant in this instance is approximately six degrees.

FIG. 8 shows an Ankylos implant with a Ridge Lap coronal configuration 105 placed in an immediate extraction socket 96 again reflecting the Ankylos placement protocol of submerging the implant approximately 2.0 millimeters 97 below the most apical crestal bone level 98. Bone crests 98 and 99 show bone growing over the shoulder of the implant but in this configuration the bone on the lingual aspect is shown growing over the shoulder of the implant at a more coronal level. The dimension 102 in FIG. 8 is less than the distance 100 in FIG. 7 representing that a more coronal level of lingual bone being maintained. The dimension 103 in FIG. 8 shows the greater height of interproximal bone level being maintained using the Ridge Lap configuration 105.

Figure 9:
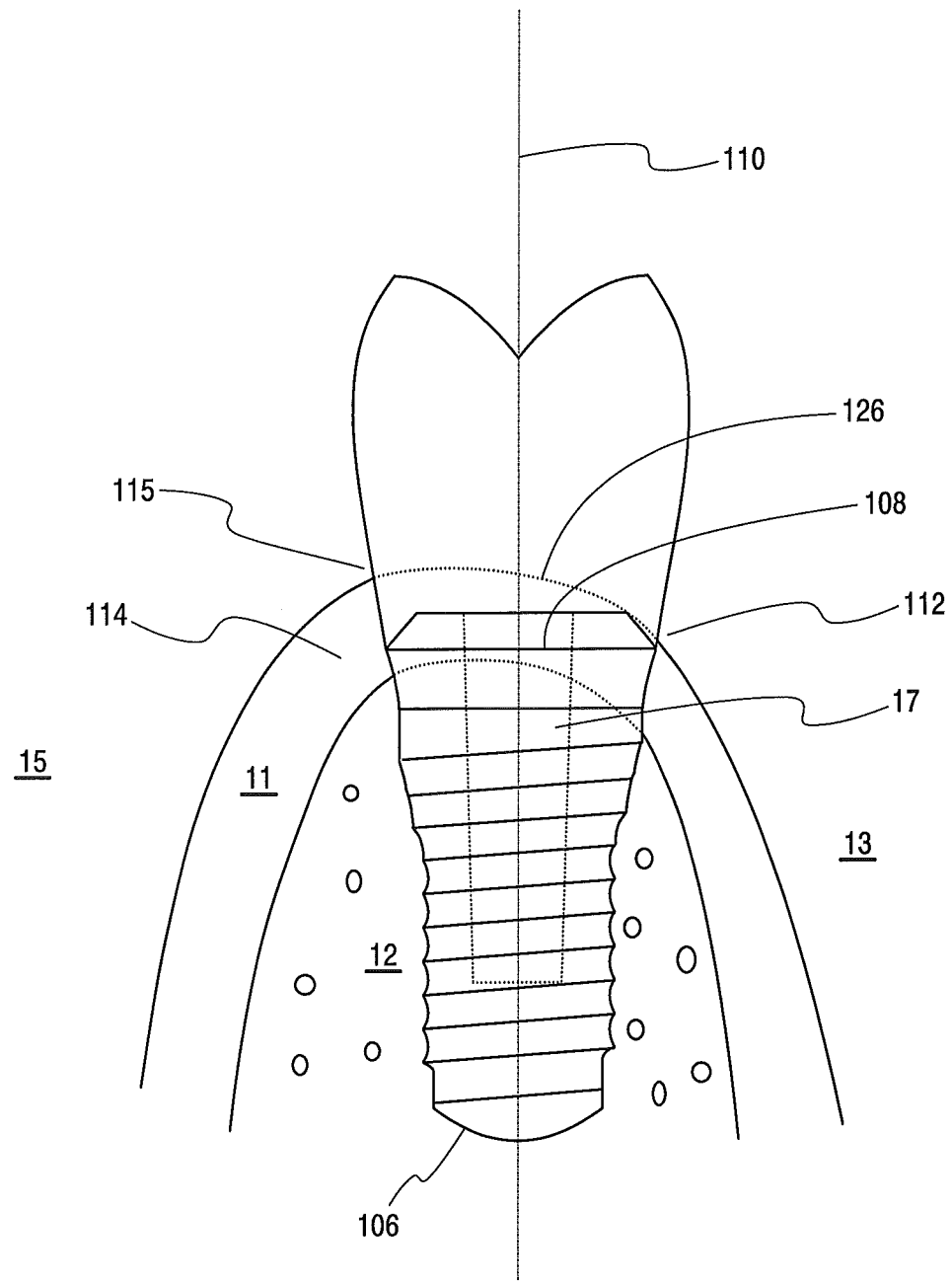
FIG. 9 is a cross sectional view of a prior art single implant with a flat top reflecting the Straumann coronal configuration.

FIG. 9 shows a single stage implant 106 of the Straumann type implanted in the jawbone 12 as often found in the lower posterior region after tooth loss and bone remodeling. The coronal contour 108 is flat and perpendicular to the fixture long axis 110. The top of the fixture is shown relatively level with the soft tissue 112 on the buccal aspect 13 and the corresponding lingual level is shown submerged 114 below the soft tissue level 115 on the generally lingual aspect.

Figure 10:
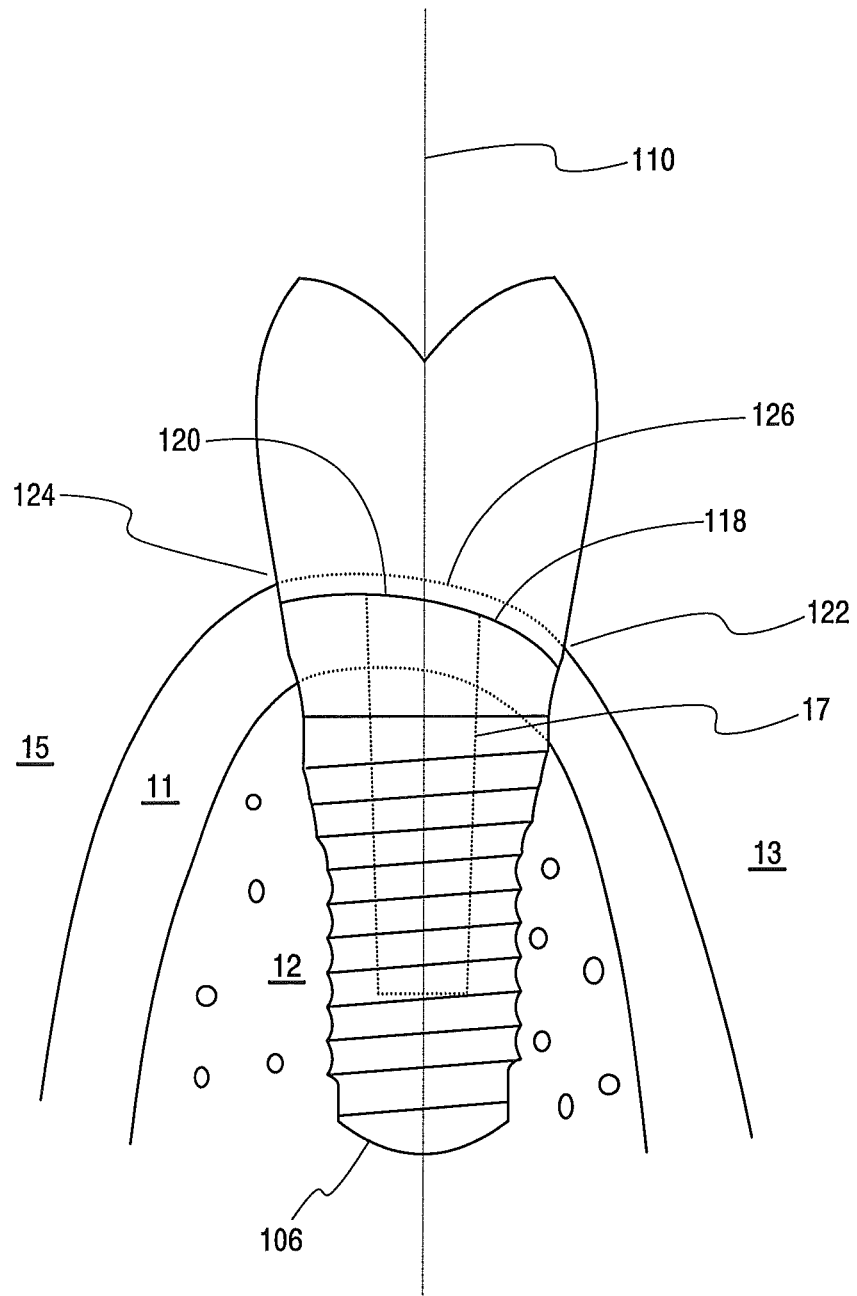
FIG. 10 is a cross section view of a Straumann type single stage implant with a coronal Ridge Lap contour shown more ideally following the soft tissue contour present in the lower posterior region of the mouth.

FIG. 10 shows a single stage implant 116 of the Straumann type implanted in the jawbone 12 as often found in the lower posterior region after tooth loss and bone remodeling but reflecting the Ridge Lap coronal configuration 118. The coronal contour is convex 120 compared to the long axis 110 in this side view shown and the top of the fixture is shown relatively level with the soft tissue 122 on the buccal aspect 13 and the corresponding lingual level shown again relatively level with the soft tissue 124 on the lingual aspect 15. Clearly the top 118 of the single stage implant with the Ridge Lap configuration in FIG. 10 follows the coronal soft tissue contours 126 much more ideally than the flat top 108 of the single stage implant 106 of FIG. 9.

Figure 11:
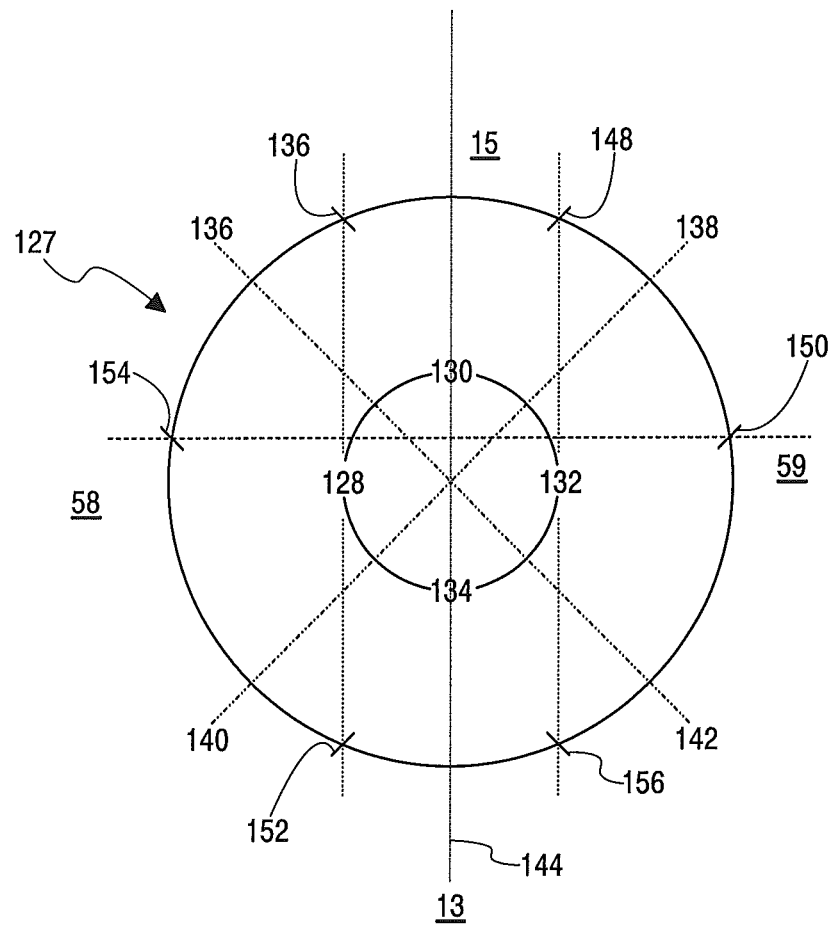
FIG. 11 is a top view of an Ankylos type design describing the various sides when positioned in the mouth.

FIG. 11 is an illustration of most adjacent lengths. Implants once imbedded in the jawbone have mesial, distal, buccal and lingual orientation sides. Since most implants have a flat coronal configuration the lengths on all sides are equal. However, when the top or coronal aspect of an implant is contoured the lengths become unequal. Looking down at the top of the implant 127 in FIG. 11 the four sides, namely the mesial 58, distal 59, buccal 13 and lingual 15 are represented by ninety 90 degree divisions 128, 130, 132 and 134. The point 136 would represent the most adjacent mesial length for all lingual lengths and point 138 would be the location of the most adjacent distal length for all the lingual lengths. The point 140 would represent the most adjacent mesial length and the point 142 would be the location of the most adjacent distal length for all buccal lengths.

The top view of FIG. 11 is further illustrative of the relationship between the positions about the sides of the implant. In particular, the midline or centerline 144 cuts between the mesial 58 and distal 59 sides. Corresponding mirror image lingual lengths 146 and 148 are shown on the lingual side 15. Similarly, corresponding mirror image buccal lengths 152 and 156 are shown on the buccal side 13. Accordingly, the corresponding lingual and buccal lengths are those points (146/152 and 148/144) across the top view. Similarly, the corresponding mesial and distal lengths are those points (154/150) across the top view.

The invention claimed is:

1. A two stage bone level dental implant for implanting within a human jawbone, the implant comprising:
   a longitudinal body having an outer bone engaging surface, an apical end, a coronal end and mesial, distal, buccal and lingual sides;
   said body having lengths along said outer surface between said apical and coronal ends such that when positioned in the jawbone said body includes mesial lengths, distal lengths, buccal lengths and lingual lengths;
   said coronal end having an inner female conical shape, said coronal end having a coronal bevel having proximal aspects and distal aspects, said coronal bevel having a bone engaging contour defined by said distal aspects of said coronal bevel, and said coronal bone engaging contour is contoured to provide a continuous asymmetric coronal contour without any abrupt changes in direction such that the longest mesial and distal lengths are equal, the buccal lengths are shorter than their most adjacent mesial and distal lengths and the lingual lengths are shorter than their most adjacent mesial and distal lengths such that the shortest lingual length is longer than the shortest buccal length; and
   when viewed from the mesial or distal aspects said bone engaging coronal contour is convex without abrupt interruption in direction from a most lingual point to a most buccal point.

2. A bone level dental implant for implanting within a human jawbone at or below the bony crest, the implant comprising:
   a longitudinal body having an outer bone engaging surface, an apical end, a coronal end and mesial, distal, buccal and lingual sides;
   said body having lengths along said outer surface between said apical and coronal ends such that when positioned in the jawbone said body includes mesial lengths, distal lengths, buccal lengths and lingual lengths;
   said coronal end having a coronal bevel having proximal aspect and distal aspects, said coronal bevel having a bone engaging contour defined by said distal aspects of said coronal bevel, and said coronal bone engaging contour is contoured to provide a continuous asymmetric coronal contour without any abrupt changes in direction such that the longest mesial and distal lengths are equal, the buccal lengths are shorter than their most adjacent mesial and distal lengths and the lingual lengths are shorter than their most adjacent mesial and distal lengths such that the shortest lingual length is longer than the shortest buccal length; and when viewed from the mesial or distal aspects said bone engaging coronal contour is convex without abrupt interruption in direction from most lingual point to a most buccal point.

3. A two stage bone level dental implant for implanting within a human jawbone at or below the bony crest, the implant comprising:

a longitudinal body having an outer bone engaging surface, an apical end, a coronal end and mesial, distal, buccal and lingual sides;

said body having lengths along said outer surface between said apical and coronal ends such that when positioned in the jawbone said body includes mesial lengths, distal lengths, buccal lengths and lingual lengths;

said coronal end is contoured to provide a continuous asymmetric coronal contour without any abrupt changes in direction such that the longest mesial and distal lengths are equal, the buccal lengths are shorter than their most adjacent mesial and distal lengths and the lingual lengths are shorter than their most adjacent mesial and distal lengths such that the shortest lingual length is longer than the shortest buccal length; and when viewed from the mesial or distal aspects said bone engaging coronal contour is convex without abrupt interruption in direction from a most lingual point to a most buccal point.

4. The dental implant of claim 2 or 3 wherein said coronal end further having an inner female conical shape to accept an abutment.

5. A one stage bone level dental implant for implanting within a human jawbone, the implant comprising:

a longitudinal body having an outer bone engaging surface, an apical end, a coronal end and mesial, distal, buccal and lingual sides;

said body having lengths along said outer surface between said apical and coronal ends such that when positioned in the jawbone said body includes mesial lengths, distal lengths, buccal lengths and lingual lengths;

said coronal end having an inner female conical shape, said coronal end is contoured to provide a continuous asymmetric coronal contour without any abrupt changes in direction such that the longest mesial and distal lengths are equal, the buccal lengths are shorter than their most adjacent mesial and distal lengths and the lingual lengths are shorter than their most adjacent mesial and distal lengths such that the shortest lingual length is longer than the shortest buccal length; and when viewed from the mesial and distal aspects said coronal contour is convex without abrupt interruption in direction from a most lingual point to a most buccal point.

6. A dental implant of claim 1, 2, 3, or 5, wherein said body is substantially circular.

7. A dental implant of claim 1, 2, 3, or 5, further comprising a circumferentially oriented textured surface.

8. A dental implant of claim 7, wherein said circumferentially oriented texture surface comprises circumferential grooves.

9. A dental implant of claim 7, wherein said circumferentially oriented texture surface comprises micro-threads near said coronal end.

10. A dental implant of claim 9, further comprising threads near said apical end.

11. A dental implant of claim 10, wherein said threads are deeper than said micro-threads.

12. A dental implant of claim 10, wherein said threads are larger than said micro-threads.

13. A dental implant of claim 9 wherein said micro-threads are of the same pitch as the larger apical threads.

14. A dental implant of claim 9, wherein said micro-threads are bone engaging micro-threads.

\* \* \* \* \*